United States Patent [19]

Craighead

[11] Patent Number: 4,640,289
[45] Date of Patent: Feb. 3, 1987

[54] BIOMEDICAL ELECTRODE

[75] Inventor: Lawrence W. Craighead, Mendota Heights, Minn.

[73] Assignee: Minnesota Mining and Manufacturing Company, St. Paul, Minn.

[21] Appl. No.: 551,069

[22] Filed: Nov. 14, 1983

[51] Int. Cl.⁴ .............................................. A61B 5/04
[52] U.S. Cl. ...................................... 128/639; 128/798
[58] Field of Search ............... 128/639, 640, 641, 644, 128/795, 796, 798, 799, 802

[56] References Cited

U.S. PATENT DOCUMENTS

| | | | |
|---|---|---|---|
| 3,805,769 | 4/1974 | Sessions | 128/2.06 E |
| 3,841,312 | 10/1974 | Corasanti | 128/2.06 E |
| 3,977,392 | 8/1976 | Manley | 128/641 |
| 3,993,049 | 11/1976 | Kater | 128/640 |
| 4,029,086 | 6/1977 | Corasanti | 128/2.06 E |
| 4,117,846 | 10/1978 | Williams | 128/303.13 |
| 4,267,840 | 5/1981 | Lazar et al. | 128/798 |
| 4,273,135 | 6/1981 | Larimore et al. | 128/640 |
| 4,300,575 | 11/1981 | Wilson | 128/798 |
| 4,393,584 | 7/1983 | Bare et al. | 29/825 |
| 4,409,981 | 10/1983 | Lundberg | 128/640 |

*Primary Examiner*—William E. Kamm
*Attorney, Agent, or Firm*—Donald M. Sell; James A. Smith; Mary M. Allen

[57] ABSTRACT

A biomedical electrode comprised of an electrical terminal member, an ionically conductive layer, a retainer sheet and a medical tape is provided. The base of the electrical terminal member is disposed between the retainer sheet and the ionically conductive layer so that the retainer sheet prevents dislodging of the terminal member upon connection and disconnection of a lead wire.

7 Claims, 5 Drawing Figures

BIOMEDICAL ELECTRODE

BACKGROUND

The invention relates to the field of disposable biomedical electrodes for establishing an electrical connection between the skin of the human anatomy and an electromedical apparatus such as a high impedance electromyograph, electrocardiograph, electrostimulator for pain relief and the like.

Many types of disposable biomedical electrodes have been introduced in recent years. Typically they comprise (1) a metallic or electrically-conductive carbon terminal member having means for electrical connection to an electromedical apparatus such as an electrocardiograph; (2) an adhesive tape or pad for holding the terminal member in place on the skin; and (3) an electrically-conductive, conformable interfacing material such as an electrolyte gel or paste over the surface of the terminal member which contacts the skin to reduce skin impedance and improve electrical contact between the skin and the terminal member.

Disposable biomedical electrodes have been improved in the last few years by the introduction of electrically conductive pressure-sensitive adhesives to replace conventional electrolyte gels and creams. Such gels are generally messy and unpleasant to use and, because of their high water content, require elaborate packaging to prevent "dry-out" problems. When an electrically-conductive pressure-sensitive adhesive is used as the interfacing material between the terminal member and the skin, a separate adhesive tape or pad to adhere the electrode to the skin may not be necessary, resulting in a smaller, lower-cost disposable electrode.

For ease of connection to the lead wire of an electromedical device, the terminal member of many disposable biomedical electrodes is formed in the shape of the male portion of a snap fastener adapted to engage the female portion of the snap fastener attached to the lead wire of the electromedical device. Such a terminal member comprises a flat, circular portion and a knob-like projection extending perpendicularly therefrom. Such a one-piece terminal member is illustrated in U.S. Pat. No. 4,273,135. A one-piece terminal member of this type is difficult to securely anchor to the adhesive pad. If the terminal member is not securely anchored to the other components of the disposable electrode, it may pull out when force is applied to disconnect the terminal member from the female portion of the snap fastener.

To avoid this problem, a two-piece terminal member is typically used comprising a so-called "stud and eyelet" arrangement. The stud comprises a flat circular portion and a pin-like member extending perpendicularly therefrom. The stud is inserted into an eyelet comprising a hollow knob having a circular base. The adhesive tape or stiffening piece used to reinforce the adhesive tape is sandwiched between the stud and the eyelet. After the stud is inserted into the eyelet, the eyelet is crimped at its neck to ensure good electrical contact between the stud and eyelet and securely anchor the adhesive tape or stiffening piece. Alternatively, the stud can be friction fitted within the eyelet without crimping.

The two-piece terminal member as described above suffers from a number of disadvantages including potential corrosion problems if the stud and eyelet are made from dissimilar metals, electrical resistance between the stud and eyelet, and increased difficulty and cost of manufacturing.

Because of the disadvantages associated with the two-piece terminal member, particularly its high cost, a number of attempts have been made to solve the anchoring problems encountered with one-piece terminal members so that the latter might be more suitable for disposable bioelectrodes.

U.S. Pat. No. 3,841,312 describes a retaining ring which fits over the projecting portion of the terminal member to mechanically secure the adhesive tape to the flat base portion of the terminal member. U.S. Pat. No. 3,993,049 discloses a bioelectrode having a one-piece terminal member which is mechanically attached to the other layers of the electrode by a swaged stiffening member. U.S. Pat. No. 4,029,086 describes a disposable bioelectrode having a one-piece terminal member in which the projecting portion thereof contains a ridge over which a washer is snapped to secure the terminal member to the adhesive pad. U.S. Pat. No. 4,117,846 describes a similar method utilizing a pair of washers to secure the terminal member to the adhesive pad.

In general, the prior art methods of anchoring the one-piece terminal member to the other components of the electrodes have involved a friction-fit washer or retaining ring which is mechanically biased against the stem of the knob-like projection of the terminal member. Although such methods of anchoring generally produce satisfactory anchoring of the terminal member to the electrode, they complicate the manufacture of the electrode and increase its cost.

The biomedical electrode of the present invention overcomes the disadvantages of the prior biomedical electrodes by securely anchoring the one-piece terminal member within the electrode without the necessity of washers or other retaining means that are mechanically biased against the projecting portion of the terminal member. This dramatically simplifies the method of manufacture of the electrode without compromising its mechanical integrity. A further aspect of the invention involves the use of a metal layer in conjunction with the anchoring means of the present invention to improve the electrical performance of the electrode and permit the use of a wide variety of ionically conductive mediums including conductive adhesives.

SUMMARY OF THE INVENTION

According to the invention, there is provided a biomedical electrode comprising (1) an electrical terminal member comprising a base having a lower major surface and an upper major surface and a post integral with the upper major surface of the base and extending therefrom, said post presenting an exposed surface for direct physical and electrical connection to a lead wire of an electromedical device; (2) a conformable, ionically conductive layer in physical and electrical contact with the lower surface of said base and extending peripherally from said base; and (3) a retainer sheet having upper and lower major surfaces bound together by an edge surface and having an aperture there through that is spaced apart from the edge surface and dimensioned to receive and to surround said post, said retainer sheet extending outwardly from said post beyond said base contacting said lower major surface of said retainer sheet and said ionically conductive layer to positionally confine said electrical terminal member between said retainer sheet and said ionically conductive layer.

The terms ionically conductive as used herein to describe the layer mean the layer is electrically conductive due to the inclusion of sufficient amounts of ionic substances as well known in the art. The term retainer as used herein to describe the retainer sheet means the sheet has sufficient structural integrity to withstand the forces encountered in normal use without the need of washers or other retaining means that are mechanically biased against the post. The retainer sheet resists tearing, stretching and the like to positionally confine the terminal member within the electrode. In use, the post of the terminal member is connected to the lead wire of the electromedical device and the conductive layer is held in contact with the skin. As the patient moves around or when the lead wire is disconnected from the terminal member, a force is applied to the terminal member. This force tends to separate the terminal member from the remainder of the electrode. The retainer sheet resists this force. It does not, for example, stretch sufficiently to allow the base to pass through the aperture in the retainer sheet. Instead, the electrode separates from the skin or the mechanical attachment of the lead wire to the terminal member is broken before the terminal member is disassociated from the remainder of the electrode.

The preferred embodiment of the disposable biomedical electrode of the present invention further comprises an electrically-conductive metal or metallized layer disposed between the retainer sheet and the upper surface of the base and also extending beyond the periphery of the base between the retainer sheet and a substantial portion of the conductive layer. It is especially preferred that this metal or metallized layer be coextensive with the retainer sheet and pre-attached thereto by vapor-deposition or other conventional coating techniques prior to assembly of the electrode. The presence of the metal or metallized layer improves conduction of electrical impulses from the skin to the terminal member.

The preferred embodiment of the disposable biomedical electrode of the invention also comprises a medical tape comprising of a backing and a pressure-sensitive adhesive coating on at least one surface thereof, the tape having an aperture therein dimensioned to recieve said post. The adhesive coated surface of the tape contacts the retaining sheet and extends beyond the periphery of the retaining sheet and the ionically-conductive layer to assist in securing the electrode to the skin. This may be necessary when a cohesive conductive gel that does not exhibit sufficient adhesiveness is used as the conductive layer. In the preferred embodiment, the ionically conductive layer is comprised of a pressure-sensitive, electrically conductive adhesive, and the medical tape is not required, although preferred.

Protective release liners are also included in the disposable electrode to protect the conductive layer and the adhesive-coated surface of the tape prior to application of the electrode to the skin.

Furthermore, in the preferred embodiment of the electrode, electric current is conducted simultaneously through the conductive layer to the terminal member and through the metal or metallized layer to the terminal member. This increases the overall electrical sensitivity of the electrode and reduces the criticality of the nature of the conductive layer utilized. More particularly, since a large portion of the electric current travels a significant portion of the distance from the underlying skin to the terminal member through a near-perfect conductor, i.e., the metal or metallized layer, the overall electric noise within the electrode is significantly reduced.

BRIEF DESCRIPTION OF THE DRAWINGS

Other advantages of the invention will become apparent from the following drawings wherein like numerals refer to like parts, the accompanying description and the appended claims.

DESCRIPTION

Figure 1:
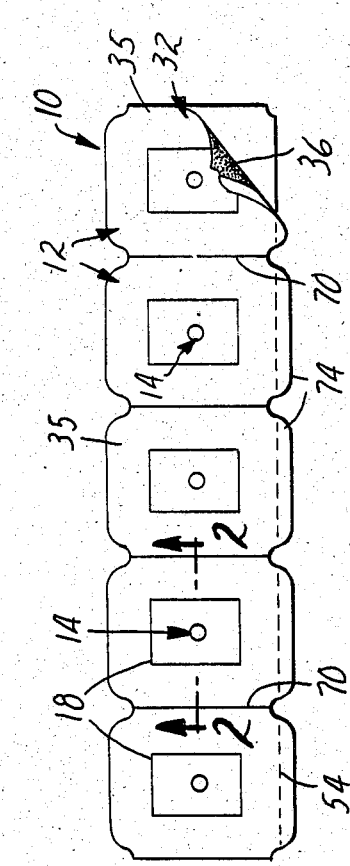
FIG. 1 is a top view of a strip of biomedical electrodes of the present invention made according to the method of the present invention.
Figure 2:
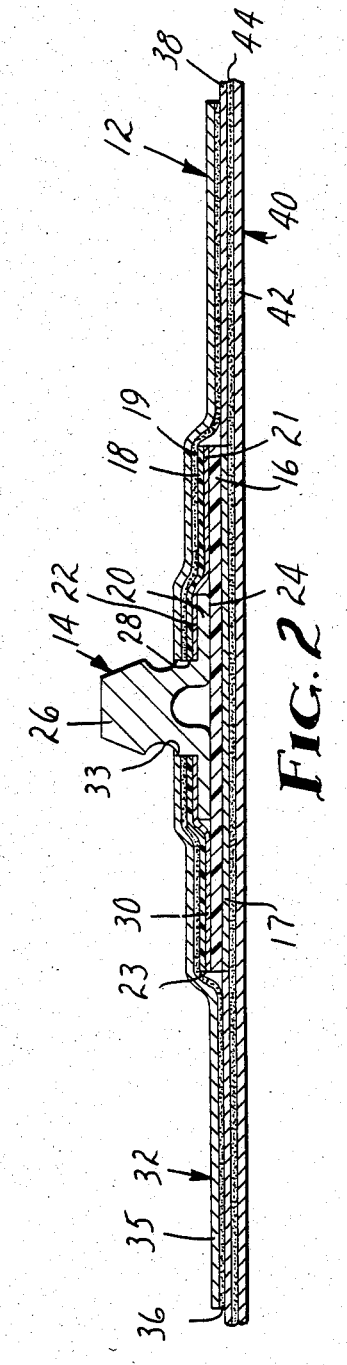
FIG. 2 is a cross-sectional view of one of electrodes shown in FIG. 1, taken along the line 2—2 of FIG. 1.

Referring now generally to the drawings and in particular to FIGS. 1 and 2, there is shown a strip 10 of biomedical electrodes 12 of the present invention made according to the method of the present invention. As shown, the electrode 12 generally comprises an electrical terminal member 14, a conformable, ionically conductive layer 16, and a retainer sheet 18. The terminal member 14 comprises a base 20 having generally coplanar upper and lower surfaces 22 and 24, respectively, and an upstanding post 26 integral with the upper surface 22 of the base 20. The post 26 is adapted for connection with a lead wire, not shown, which, in turn, is attached to the electromedical apparatus. The terminal member 14 is preferably comprised of metal or is provided with a metallized outer layer, but it can comprise other materials such as conductive carbon. The conductive layer 16 underlies and is in physical and electrical contact with the lower surface 24 of the base 20 and extends outward from the periphery thereof. The surface of the conductive layer 16 opposite that contacting the terminal member 14 is applied to the skin of the patient. A protective release liner 17 overlies the exposed surface of conductive layer 16 prior to application to the patient.

The terminal member 14 is securely retained within the electrode 12 by the retainer sheet 18. The retainer sheet 18 is comprised of an upper major surface 19 and a lower major surface 21 bound together by edge surfaces 23. The retainer sheet 18 has an aperture 28 there through spaced apart from the edge surfaces 23 and dimensioned to receive and to surround the post 26. The aperture 28 is preferably larger in diameter than the largest diameter of post 26 of the terminal member 14. The retainer sheet 18 overlies a substantial portion of the upper surface 22 of the base 20 and extends beyond the periphery of base 20 to overlie a substantial portion of layer 16.

Electrode 12 further comprises an electrically-conductive metal or metallized layer 30 which is preferably formed from the same metal as that forming the terminal member. The metal layer 30 has an aperture there through that is dimensioned to receive the post 26 and is preferably larger in diameter than the largest diameter of the post 26. Metal layer 30 is disposed between the retainer sheet 18 and the upper surface 22 of the base 20 and extends outward beyond the periphery of base 20 between the retainer sheet 18 and the conductive layer 16. Preferably metal layer 30 is coextensive with retainer sheet 18 and pre-attached thereto by vapor deposition or other conventional means. The metal layer 30 causes electrical impulses picked up on the mammalian skin to be conducted simultaneously through the ionically conductive layer 16 and through the metal layer 30 to the terminal member 14.

A number of suitable materials may be chosen for the metal layer 30. For example, the metal layer 30 can be comprised of a metal foil, e.g., silver or tin foil, or metal flakes. As noted above, the metal layer 30 is preferably directly applied to the retainer sheet 18 by conventional coating, printing or laminating techniques or the like. By utilizing the same metal for the metal layer 30 and the terminal member 14, the potential for corrosion between the interface of the metal layer 30 and the terminal member 14 is essentially eliminated.

A number of materials can be used for the retainer sheet 18. In the preferred embodiment, where retainer sheet 18 and metal layer 30 are preattached to each other, the retainer sheet 18 is comprised of a gravure printed, silver/silver chloride treated, polyester film. The polyester film is a dielectric material that can insulate the remainder of the electrode 12 from stray electrical signals that could otherwise be picked up from the surroundings including static charges from nearby clothing, bedding or the like. Other materials will work. For example, various polyethylene, polypropylene and vinyl films can be used. Another suitable material is number 57 EDP "facer only" paper available from Green Bay Packaging, Inc., P. O. Box 1107, Green Bay, Wisconsin 54305.

Similarly, a number of materials can be used for the ionically conductive layer 16. In the preferred embodiment, the layer 16 is comprised of a pressure-sensitive, conductive adhesive. Certain cohesive conductive gels will also work. Suitable gels are disclosed in U.S. Pat. No. 4,377,170 which is hereby incorporated by reference. If a non-adhesive, cohesive conductive gel is used for the layer 16, the layer 16 would have to be otherwise adhered to the retainer sheet 18. For example, the layer 16 could be satisfactorily adhered to the retainer sheet 18 by peripherally taping the layer 16 to the retainer sheet 18 with a suitable medical tape as described more fully below.

The use of the retainer sheet 18 greatly simplifies the construction of the electrode 12 without compromising the integrity of the electrical connection of the terminal member 14 with the ionically conductive layer 16. As taught by the present invention, the retainer sheet 18 intimately contacts the metal layer 30 and the base 20 of the terminal member 14 without the need for washers, retaining rings or the like which are mechanically biased against the post 26. There is no dissimilar material interposed between the metal layer 18 and the base 20 that could give rise to electrical noise. This is made possible by the inclusion of the retainer sheet 18. At the same time, the retainer sheet 18 securely holds the terminal member 14 within the electrode 12; the terminal member 14 cannot be easily pulled out in use when adapted to the lead wire.

The preferred embodiment of biomedical electrode 12 includes a medical tape 32 having an aperture 33 there through that is dimensioned to receive the post 26 and is preferably larger in diameter than the largest diameter of the post 26. The medical tape 32 is adhered to the upper major surface 19 of the retainer sheet 18 and extends outward from the periphery thereof to assist in adhering the electrode 12 to the skin. The medical tape 32 comprises a backing 35 and a suitable pressure sensitive adhesive 36 on the surface contacting the upper surface 19 of the retainer sheet 18 and the skin. A suitable medical tape is available from Minnesota Mining and Manufacturing Company, 3M Center, St. Paul, Minnesota 55144 under the trademark "Micropore".

The adhesive 36 of the medical tape 32 extending beyond the periphery of the retainer sheet 18 is adhered to a silicone-coated release liner 38 as is well known in the art. The underside of the release liner 38, in turn, is adhered to a suitable protective sheet 40 comprising a backing 42 and a pressure-sensitive adhesive 44. Protective sheet 40 is present to cover the apertures formed in the release liner 38 during the manufacture of the electrodes 12 as described below and contact protective release liner 17 over ionically conductive layer 16. Protective sheet 40 assists in the removal of the layer 16 from the release liner 17.

Figure 3:
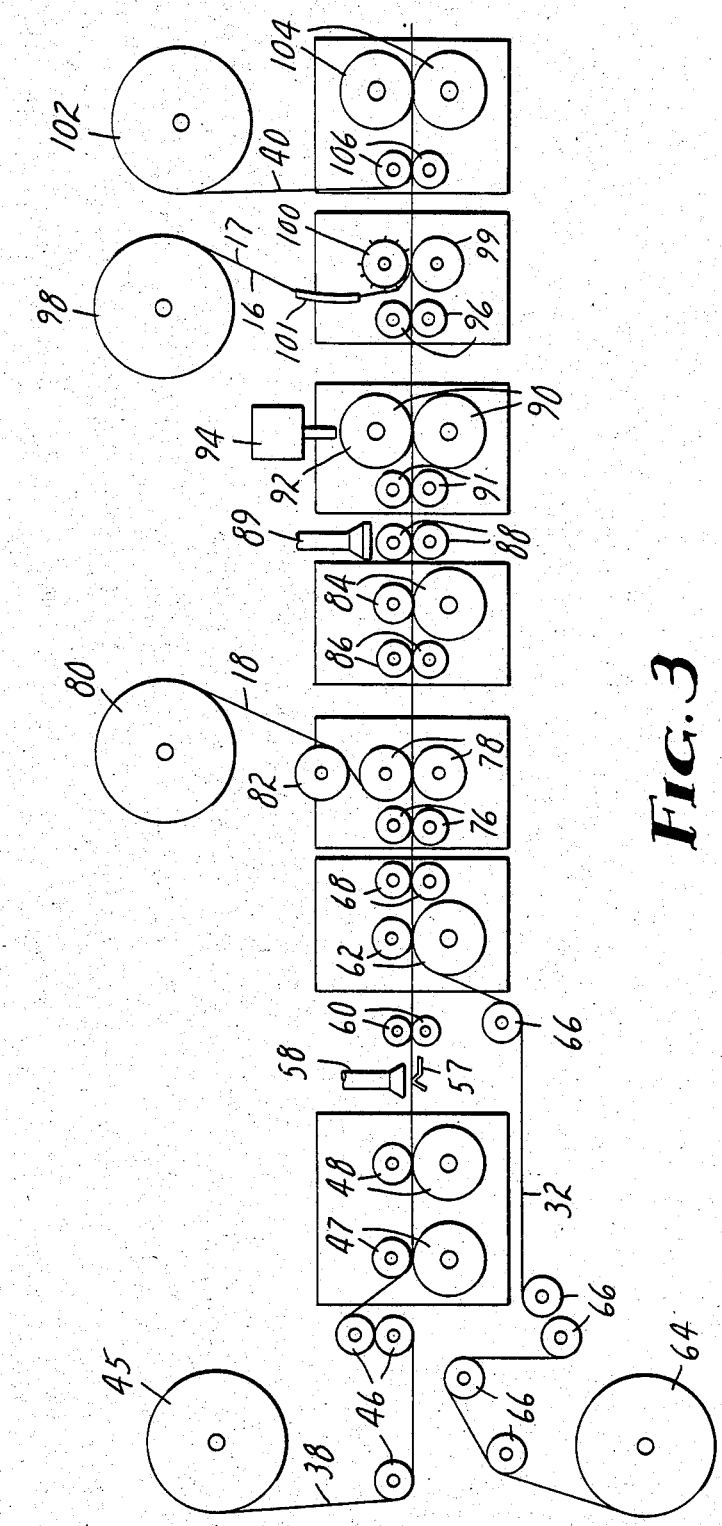
FIG. 3 is a schematic representation of a method of manufacturing the strip of biomedical electrodes of FIG. 1.
Figure 4:
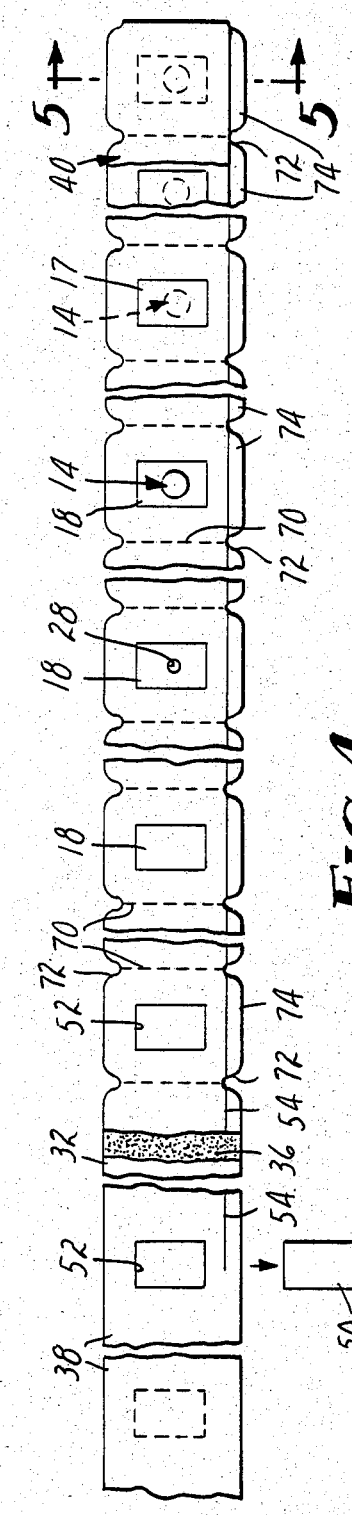
FIG. 4 is a bottom view of a strip of biomedical electrodes of the present invention being formed according to the method represented in FIG. 3.
Figure 5:
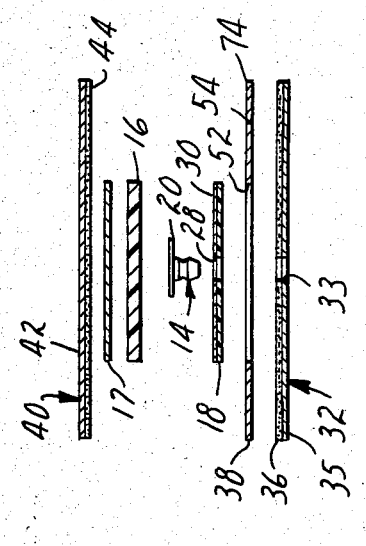
FIG. 5 is an exploded, cross-sectional view taken along 5—5 of FIG. 4.

An automated method for producing the biomedical electrode 12 will next be described in relation to FIGS. 3, 4 and 5. Referring primarily to FIG. 3, there is shown in schematic representation, a method of manufacturing the strip 10 of biomedical electrodes 12 with the use of automated equipment. As shown, the release liner 38 is stored on a roll 45. When the automated equipment is energized, the release liner 38 is pulled off the roll 45 by tension-unwind rollers 47. The release liner 38 is guided towards the rollers 47 by constant tension, unwind rollers 46.

From the rollers 47, the release liner 38 is pulled through conventional die-cutting rollers 48. The die-cutting rollers 48 die-cut the release liner 38 to form rectangularly shaped pieces 50 and apertures 52 in the release liner 38. At the same time, longitudinal cut 54 is made in the release liner 38. This is best shown in FIG. 4 and FIG. 5. The rectangularly shaped piece 50 is removed from the release liner 38 by a kicker spring 57 and a vacuum 58. The release liner 38 is guided past the vacuum 58 by rollers 60.

Once the apertures 52 are formed in the release liner 38, the medical tape 32 is adhered to the release liner 38 by laminating rollers 62. As noted earlier, the medical tape can be "Micropore" brand medical tape. A suitable width for the medical tape 32 and for the release liner 38 is 3½ inches (8.89 cm). A suitable adhesive weight for the medical tape 32 is 6 to 12 grains.

The medical tape 32 is stored on a roll 64. When the automated equipment is energized, the medical tape 32 is pulled and guided towards the laminating rollers 62 by rollers 66.

After the medical tape 32 is laminated to the release liner 38, the outlines of the individual electrodes 12 are formed on the medical tape 32 by conventional die-cutting rollers 68. The die-cutting rollers 68 make controlled-depth cuts 70 in the medical tape 32 and remove indentations 72 in medical tape 32 and in release liner 38 to form tabs 74. This is best shown in FIG. 4. Through the use of controlled-depth cutting with the rollers 68, the cuts 70 in the medical tape 32 are made without cutting the release liner 38. The tabs 74 facilitate removal of the individual electrodes 12 from release liner 38 and will be later explained in conjunction with the use of the electrodes 12.

After the individual electrodes 12 are outlined on the medical tape 32, the strip 10 is pulled and guided by rollers 76 to die-cutting and laminating rollers 78. The rollers 78 laminate the retainer sheets 18 to the medical tape 32. Retainer sheets 18 are cut from roll 80. The sheeting material is pulled from roll 80 by a roller 82 and guided to the die-cutting and laminating rollers 78. The upper roller 78 transversely cuts the sheeting material into lengths forming retainer sheets 18 and carries the sheets 18 down to the lower roller 78 where the individual sheets 18 are adhered to the medical tape 32 through the apertures 52 in the release liner 38. In the preferred embodiment, the electrically conductive metal layer 30 is already adhered to the sheeting material on the roll 80. This can be accomplished by coating, printing or laminating the sheeting material with the metal or metallized layer 30 as already described. As the sheeting material is unrolled from the roll 80, metal layer 30 is cut with the retainer sheet 18, and the combination is adhered to the medical tape 32.

From the foregoing, it is clear that the inclusion of the metal layer 30 can be made optional. Exclusion of the metal layer 30 will generally result in higher electrode impedances depending upon the exact conductive adhesive 16 employed, but satisfactory performance can still be achieved by well-known techniques.

Next, the aperture 28 in the retainer sheet 18 is formed by die-cutting rollers 84. The strip 10 is pulled and guided in the rollers 84 by rollers 86. Die-cutting rollers 84 extend the aperture 28 in retainer sheet 18 on through the medical tape 32 to form the aperture 33. This is best seen in FIG. 4 and FIG. 5. The strip 10 is pulled from the rollers 84 and guided on through the automatic equipment by rollers 88. At rollers 88, loose material resulting from the extension of the aperture 28 through the medical tape 32 to form the aperture 33 is removed by the vacuum 89.

The strip 10 is fed to the rollers 90 by the rollers 91. At rollers 90, the terminal members are placed within the apertures 28 and 33 by a vacuum placement system 92 within the upper roller 90. As described earlier, when the terminal members 14 are placed within the apertures 28 and 33, the upper major surface 22 of the base base 20 is contacted with the lower surface of metal layer 30. The terminal members 14 are fed to the vacuum placement system 92 by a vibratory feeder 94 available from Rockford Feeder Co., 5061 Contractors Drive, Rockford, Illinois 61111.

After the terminal members 14 are properly located, the strip 10 is again pulled and guided to the next operation by a pair of rollers 96. The next operation comprises the addition of the ionically conductive layer 16. The sheeting material from which the layers 16 are cut is stored on a roll 98. One major surface of the layer 16 is covered with a silicone-coated protective release liner 17 similar to the release liner 38. The release liner 17 is shown in FIG. 2 and in FIG. 5. It serves two purposes. Firstly, it prevents the layer 16 from sticking to itself on the roll 98. This is especially important when the layer 16 is comprised of the pressure-sensitive, conductive adhesive described earlier. Additionally, the release liner 17 protects the layer 16 after the electrode 12 is fully manufactured and until the electrode 12 is applied to the skin.

The layer 16 and the release liner 17 are guided to die-cutting and laminating rollers 99 and 100 by a guide 101. The roller 100 can have an internal vacuum system that holds layer 16 and release liner 17 against the roller 100 until cut to approximately the size and shape of the aperture 52 in the release liner 38. The rollers 99 and 100 also adhere the lower major surface of the metal layer 30 to the upper surface of the conductive adhesive layer 16 through the aperture 52 in the release liner 38.

The release liner 17 is secured to the release liner 38 by the protective sheet 40 from a roll 102. As described earlier, the protective sheet 40 is comprised of the suitable backing material 42 and the pressure-sensitive adhesive 44. It is shown in FIG. 2 and FIG. 5.

Finally, the strip 10 is guided to die-cutting rollers 104 by rollers 106 where it is cut into suitable lengths of strips 10 by the die-cutting rollers 104. At the same time, the individual electrodes 12 can be made separable by perforating the release liner 38 along each of the cuts 70 in the medical tape 32. The result is the strip 10 of biomedical electrodes 12 shown in FIG. 1.

The strips 10 of the electrodes 12 are sealed in suitable protective, clean packages prior to shipment to the end users. The electrodes 12 are used by pulling the individual electrodes 12 away from the release liner 38 with the aid of the tabs 74 and applying the electrodes 12 to the patient as prescribed by qualified medical personnel. The materials chosen for the medical tape 32, the release liners 38 and 17 and the layer 16 are such that the bond between medical tape 32 and the release liner 38 and the bond between the conductive layer 16 and the release liner 17 are broken to allow the electrode 12 to be peeled away from the rest of the strip 10 so that the electrode 12 can be applied to the patient. These material characteristics are conventional and well known in the art.

Using the above-described method, five electrodes of the present invention were made to include the following:

EXAMPLE 1

"Scotchpar" brand polyester film, available from Minnesota Mining and Manufacturing Company, was adhered to six-grain, "Micropore" medical tape. The polyester film included a $5 \times 10^{-4}$ centimeters thick layer of #5005 silver composition ink available from E. I. Du Pont De Nemours, Company, Inc., 1007 Market Street, Wilmington, DE 19898. An aperture having a diameter of 0.41 centimeters was die cut through the center of the medical tape and polyester film lamination. A terminal member having a 0.41 centimeters diameter post and a 0.86 centimeters diameter base was located within the aperture. The lower surface of the base of the terminal member and the silver coated surface of the polyester film were covered with Lectron TM III, chloride-1 conductive gel available from Pharamaceutical Innovations, Inc., Newark, New Jersey 07114.

The five electrodes were tested to determine their resistance to the terminal members being pulled out or otherwise separated from the remainder of the respective electrodes using an "Instron" brand load-elongation testing instrument, Model 1122, available from the Instron Corporation, 2500 Washington Street, Canton, MA 02021. The electrodes were, one at a time, adhered to an immovable surface preprepared with 9 mm, double-coated, paper tape, #401, available from Minnesota Mining and Manufacturing Company, 3M Center, Saint Paul, MN 55144. The medical tape and the conductive gel used were adhered to the paper tape which, in turn, was adhered to a stainless steel plate. The stainless steel plate was rigidly attached to the testing instrument. The purpose of the paper tape was to insure that the medical tape and the conductive gel used did not separate from the stainless steel plate when force was applied to the terminal member.

Next, the post of the terminal member was grasped by a jaw of the testing instrument and pulled in an upward direction generally perpendicular to the plane of the electrode until the terminal member pulled out or otherwise separated from the rest of the electrode. For this test, the testing instrument was set at 100 mm per minute crosshead elongation speed.

The test results are recorded in Table 1. Also in Table 1 is recorded the results of separating the terminal members of five electrodes made the same as the five of Example 1 except that the polyester film and silver composition ink were eliminated. Also in Table 1, are the results of subjecting commercially available monitoring electrodes to the same test procedure. In each case, five electrodes were tested. In each case, the mean separation force in pounds is recorded.

TABLE 1

| Electrode | Mean Terminal Member Separation Force Exhibited in Pounds |
| --- | --- |
| Example 1 Electrodes | 19.3 |
| Example 1 Electrodes minus polyester film | 4.7 |
| "Red Dot" brand Monitoring Electrodes #2249 | 10.2 |
| "AMI" brand Monitoring Electrodes #1501-003 | 11.1 |
| "CON-MED" Monitoring Electrodes #934 | 5.7 |

In Table 1, the Red Dot electrodes are available from Minnesota Mining and Manufacturing Company, 3M Center, Saint Paul, MN 55144. The AMI electrodes are available from Andover Medical Incorporated, Lowell, MA 01852. The CON-MED electrodes are available from Consolidated Medical Equipment, Inc., 10 Hopper Street, Utica, NY 13501.

What is claimed is:

1. A biomedical electrode comprising:
   a. an electrical terminal member comprising a base having upper and lower surfaces and a post integral with said upper surface of said base and extending therefrom, said post presenting an exposed surface adapted for direct physical and for electrical connection to a lead wire of an electromedical device;
   b. an ionically conductive layer in physical and electrical contact with the entire lower surface of said base and extending peripherally beyond said base; and
   c. a conformable retainer sheet having upper and lower major surfaces bound together by an edge surface, having a surface area and shape larger than that of the terminal base, and having an aperture therethrough receiving and surrounding the post, the aperture being spaced apart from the edge surface and dimensioned with a perimeter larger than the largest perimeter of the post and smaller than the largest perimeter of the base such that a portion of the lower surface of the retainer sheet contacts the upper surface of the base and the remainder of the lower surface the retainer sheet contacts the portion of the ionically conductive layer extending peripherally beyond the base to positionally confine said electrical terminal member between said retainer sheet and said ionically conductive layer; and
   d. a medical tape comprising a backing and a pressure sensitive adhesive coating on at least one major surface thereof, the tape having an aperture therethrough receiving and surrounding said post, the aperture being dimensioned with a perimeter larger than the largest perimeter of the post and smaller than the perimeter of the retainer sheet, a portion of the adhesive-coated surface being adhered to the upper surface of the retainer sheet and the remaining portion of the adhesive-coated surface extending beyond the peripheral edges of the retainer sheet and the ionically conductive layer to assist in securing the electrode to skin.

2. The electrode according to claim 1 further comprising a conformable electrically-conductive metal or metallized layer having a surface area and shape larger than that of the lower surface of the base and having an aperture therethrough, the aperture surrounding the post and being spaced away from the edges of the metal layer or metalized layer and dimensioned with a perimeter larger than the largest perimeter of the post and smaller than the perimeter of the base, the metal layer or metallized layer being disposed between said retainer sheet and said upper surface of said base and extending beyond the periphery of the base, the conformable metal or metallized layer being in direct electrical contact with the upper surface of the base and the ionically conductive layer.

3. The electrode according to claim 2 wherein said terminal member comprises a metal or metallized member and wherein said metal or metallized layer comprises the same metal as the comprising the terminal which the layer contacts at the upper surface of its base.

4. The electrode of claim 2 wherein said conformable electrically-conductive metal or metallized layer is adhered to said retainer sheet.

5. The electrode according to claim 2 wherein said metal or metallized layer consists essentially of silver.

6. The electrode according to claim 5 wherein said retainer sheet is comprised of a polyester material.

7. The electrode according to claim 1 wherein the ionically conductive layer comprises a pressure sensitive, electrically-conductive adhesive.

* * * * *